(12) United States Patent
Gorsuch

(10) Patent No.: US 6,234,991 B1
(45) Date of Patent: *May 22, 2001

(54) METHOD AND APPARATUS FOR CONTINUOUS PERITONEAL CASCADE DIALYSIS AND HEMOFILTRATION (CPCD/H)

(75) Inventor: Reynolds G. Gorsuch, Yountville, CA (US)

(73) Assignee: Transvivo Inc., Napa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/382,237

(22) Filed: Aug. 24, 1999

Related U.S. Application Data

(63) Continuation of application No. 08/853,051, filed on May 8, 1997.

(51) Int. Cl.[7] ............................................. A61M 1/00
(52) U.S. Cl. ........................ 604/29; 604/5.01; 210/321.62
(58) Field of Search ........................... 604/4, 5, 29, 266; 210/321.6, 321.71, 321.62, 4.01, 5.01, 5.04

(56) References Cited

U.S. PATENT DOCUMENTS

| | | | |
|---|---|---|---|
| 5,047,020 | * 9/1991 | Hsu | 604/266 |
| 5,069,662 | * 12/1991 | Bodden | 604/4 |
| 5,301,685 | * 4/1994 | Guirguis | 604/406 |
| 5,397,354 | * 3/1995 | Wilk et al. | 604/500 |

\* cited by examiner

Primary Examiner—Anhtuan T. Nguyen
Assistant Examiner—Michael M Thompson
(74) Attorney, Agent, or Firm—Knobbe, Martens, Olson & Bear, LLP

(57) ABSTRACT

A continuous peritoneal dialysis is carried out by providing a dialyzer element having a filter membrane for being exposed within the peritoneal cavity and an interior dialysate passageway, the membrane having pores sufficient to allow diffusion of blood toxins, implanting the dialyzer element in the peritoneal cavity of a patient, infusing a transfer fluid into the patient's peritoneal cavity and continuously supplying substantially fresh dialysate fluid into interior dialysate passageway of the dialyzer element, directing the fluid along the passageway whereby it is exposed to the transfer fluid by diffusion through the membrane and whereby toxins from said transfer fluid are diffused into the dialysate in the dialyzer element to form toxic dialysate fluid, and continuously removing the toxic dialysate from said dialyzer element.

38 Claims, 7 Drawing Sheets

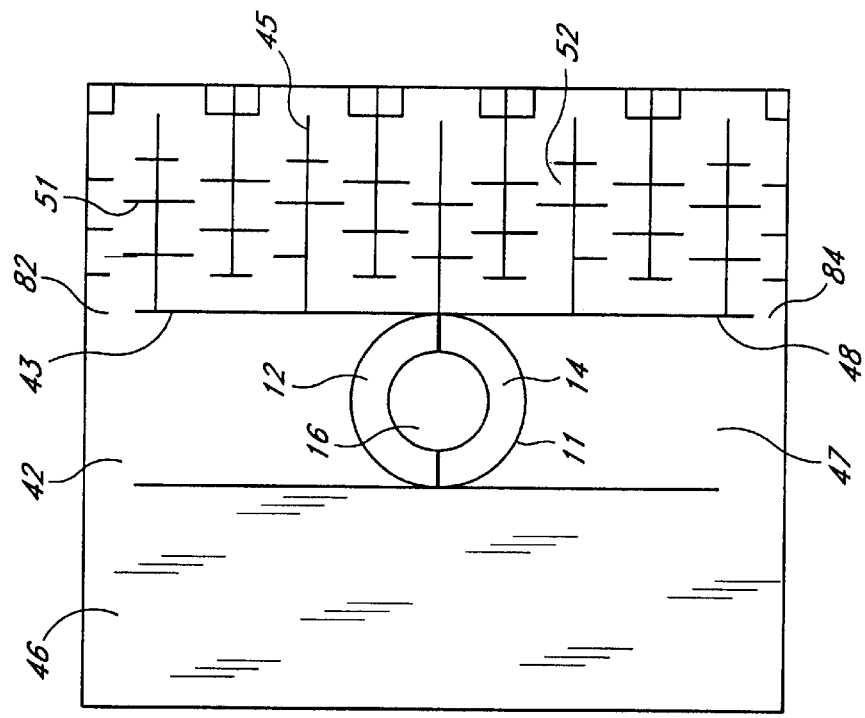

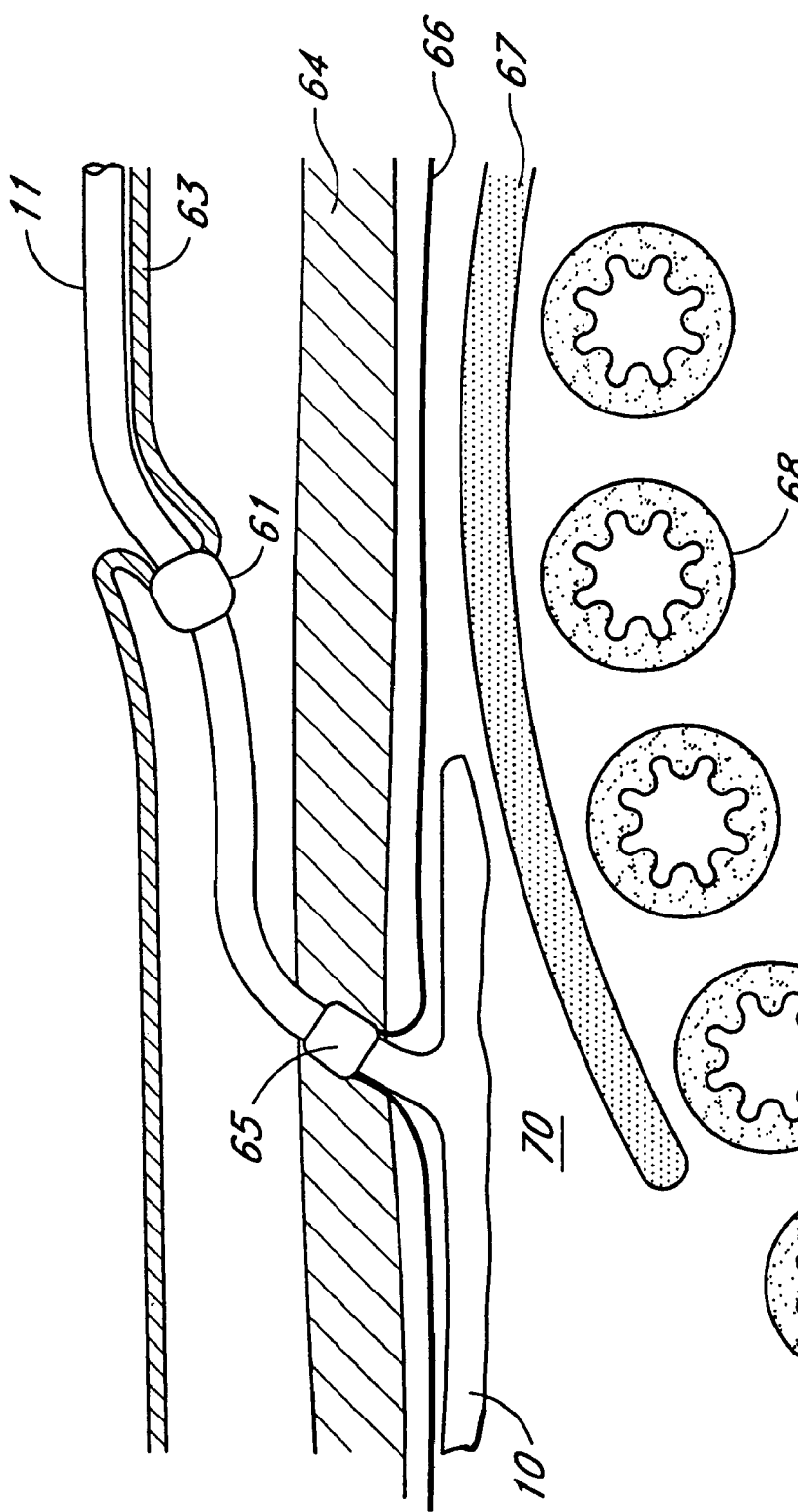

METHOD AND APPARATUS FOR CONTINUOUS PERITONEAL CASCADE DIALYSIS AND HEMOFILTRATION (CPCD/H)

This application is a continuation of application Ser. No. 08/853,051, filed May 8, 1997.

BACKGROUND OF THE INVENTION

Current medical treatment for human kidney failure includes kidney transplant, hemodialysis and peritoneal dialysis. In hemodialysis therapy, the patient's vasculature is accessed using needles, catheters or implanted artificial or surgically created arterial-venous shunts. Using such apparatus, whole blood is removed from the body and routed through an ex-vivo dialysis filter which removes catabolic and metabolic toxins by diffusion to a liquid medium or dialysate. The filtered blood is returned to the body via the access devices. Such hemodialysis is commonly performed 2–4 hours per day, 2–3 times per week resulting in a high and low blood toxin concentrations of the patient with attendant periods of trauma.

In peritoneal dialysis heretofore, using a batch process, a catheter is surgically placed in a patient's peritoneal cavity between the parietal peritoneum and the visceral peritoneum. Dialysate fluid is infused into the peritoneal cavity for a dwell time deemed adequate for being equilibrated, by diffusion, with the blood contained in the surrounding peritoneal membrane vasculature. The toxins in the patient's blood diffuse through the peritoneal membrane into the dialysate and the resulting toxin laden dialysate is then drained from the peritoneal cavity and either discarded or regenerated. Such a batch process cycling is repeated using new or fresh dialysate which is infused into the patient's peritoneum.

The peritoneal membranes act as a plasmapheresis filter which passes blood components and fluids below $10^5$ daltons from the vasculature in the membranes to the peritoneal cavity. A major disadvantage of the batch peritoneal dialysis process is that it not only removes the undesirable uric acid, urea and creatinine toxins along with other blood toxins having a molecular weight of less than $10^5$ daltons, but also many desirable proteins and other blood and plasma components. Of special concern is the removal of albumin which has a molecular weight of $6.9 \times 10^4$ as well as a number of other important and desirable blood components. Removable of substantial or excessive amounts of albumin requires replacement in order to avoid hypoalbuminemia. The expense of such albumin replacement is often quite high. In addition, the aforesaid batch peritoneal dialysis process also removes important immune system proteins. Another major disadvantage of the batch dialysis process is that each treatment requires breaking the sterile bacterial and viral barrier between the patient's body and ex-vivo thereby substantially increasing the risk of infection and contamination each time dialysis fluid is added or removed. Yet another disadvantage of the batch process is the inefficiency of the dialysis/time ratio in the process cycle since dialysis occurs only 30 minutes out of each 70 minute cycle with the remainder 40 minutes spent draining toxic dialysate and infusing fresh dialysate. It is to the elimination of such disadvantages that the present invention is directed.

SUMMARY OF THE INVENTION

The present invention is a method for carrying out continuous peritoneal dialysis using an effective dialyzer element implanted in the peritoneal cavity of a patient. Fresh dialysate is continuously supplied to the dialyzer element and toxic dialysate is continuously removed from the element during the process. The implanted dialyzer element consists of a filter membrane which is exposed to dialysate transfer medium fluid in the peritoneal cavity. A transfer medium composed of fresh dialysate fluid is infused into the peritoneal cavity where, over time, it equilibrates by diffusion with the blood in the capillaries residing in the peritoneal membranes. Fresh dialysate continuously infused into the dialyzer element comes into diffusive contact with the transfer medium and gradually becomes saturated with the toxins which diffuse from the infused dialysate transfer fluid in the peritoneal cavity through the membrane pores. The invention includes the apparatus for carrying out the aforesaid continuous peritoneal dialysis, which apparatus includes the dialyzer element and its supporting components and features for directing dialysate fluid to and from the dialyzer element. These components as well as the method and advantages of the continuous peritoneal dialysis of the invention will be described in more detail hereinafter.

BRIEF DESCRIPTION OF THE DRAWINGS

FIG. 6 is a side view and FIG. 7 a top view of another dialyzer element embodiment incorporating sheet membranes;

FIG. 10 shows the placement of a dialysis catheter through a patient's epidermis and peritoneum;

DETAILED DESCRIPTION OF THE INVENTION

Two of the most important functions of the human kidney are the removal of toxins generated by catabolism and metabolism and the elimination of excess body water. The toxins are presently considered to be largely of nitrogenous origin, primarily uric acid, urea and creatinine. These toxins originate in the cells of the body and are distributed in three basic fluid compartments: the intercellular space, the intrastitial space and the blood plasma. The toxins conveyed to the kidney by the blood where they are filtered and concentrated into the urine and excreted along with excess body fluid. Other plasma proteins are sometimes considered to be toxins when present in excess concentration, e.g., Beta-2 microglobulin. In addition to delivering these toxins to the kidney, the blood also delivers toxins the liver and the peritoneal cavity via the capillaries or vasculature in the peritoneum.

The peritoneum consists of the parietal peritoneum which lines the inner surface of the abdominal and pelvic walls including the diaphragm, and the visceral peritoneum which covers the visceral organs and forms the omentum, and the visceral mesentery, which connects the loops of the bowel. The visceral peritoneum forms a complex of several sacks in the abdomen surrounding the digestive and other organs. The peritoneum typically contains only about 100 ml of fluid, so it is normally collapsed. The total peritoneum surface area for an adult is estimated to be between about 1.18 and about 2.2 m$^2$, correlating to the mean body surface area of 2.2 m$^2$. Children having a proportionally larger peritoneal area than adults. The peritoneal membranes act as a plasmapheresis filter passing blood and plasma components below 10$^5$ daltons from the vasculature in the membranes to the peritoneal cavity. A list of blood and plasma components sized by molecular weight in daltons is disclosed in Table 1.

Figure 1:
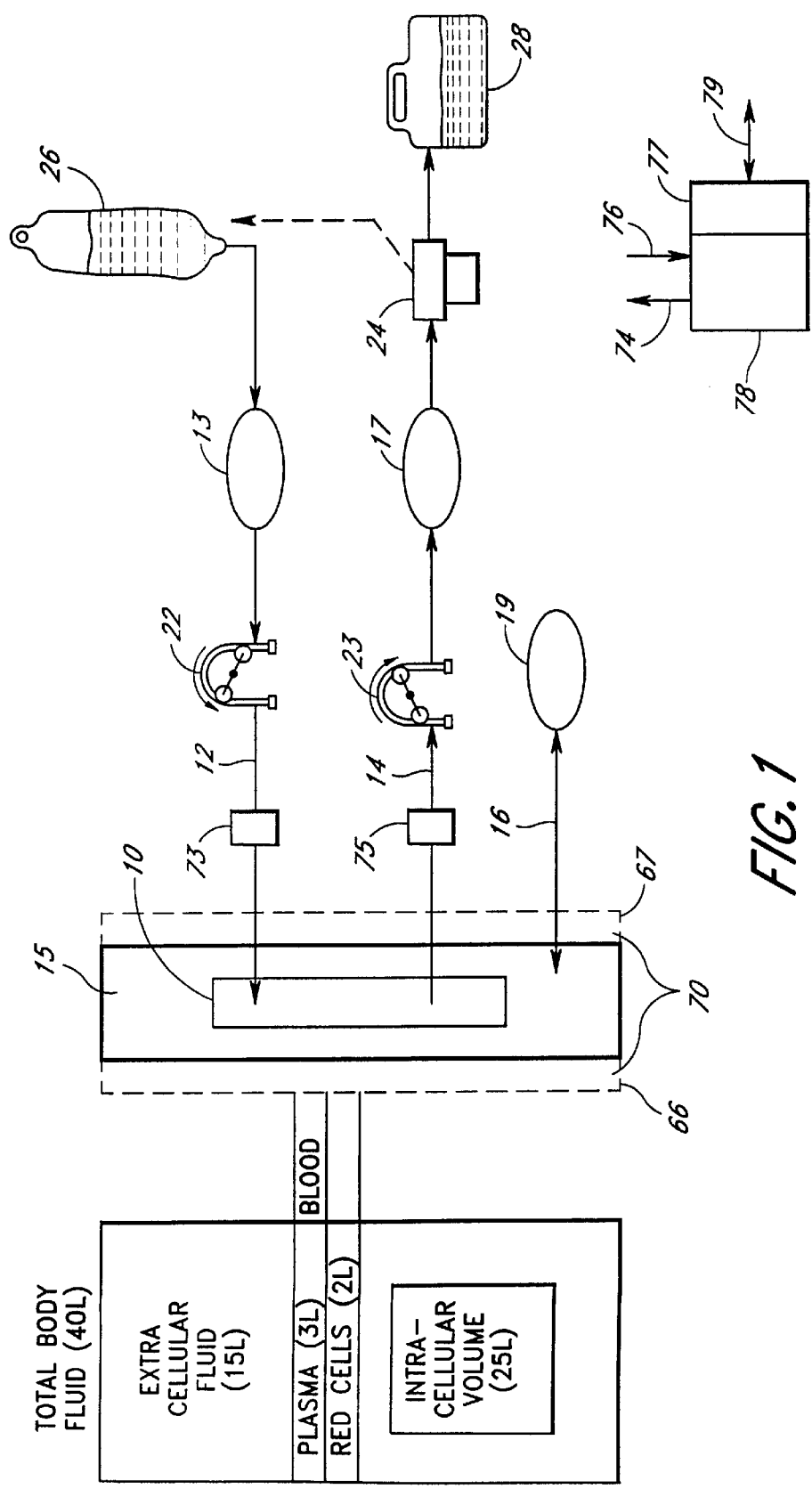
FIG. 1 is a schematic illustration of the system and apparatus used in the continuous peritoneal dialysis of the invention.
Figure 11:
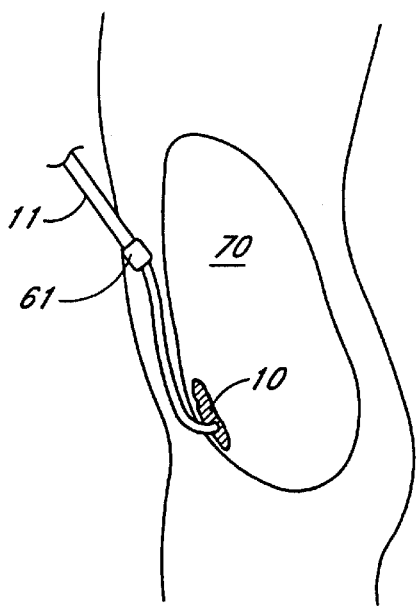
FIGS. 11, 12 and 13 illustrate the position of the dialyzer elements implanted in a patient's peritoneum.

Referring to FIGS. 1, 10 and 11, in practicing the present invention, a dialyzer element 10 is implanted in the peritoneal space 70 into which also is infused a transfer medium 15 composed of between 1.5 and 3 liters of dialysate fluid. This fluid is infused into the peritoneal cavity 70 residing between the parietal peritoneum 66 and the visceral peritoneum 67 thus enlarging the normally collapsed peritoneal space. Over time, the dialysate transfer medium equilibrates with the blood in the capillaries residing in the peritoneal membranes by diffusion. Blood components having molecular weights under 9×10$^5$ which corresponds to the upper sieving coefficient cut-off of the peritoneal membranes, and includes all known toxins present in the blood, are thus diffused into the transfer medium.

Dialyzer element 10 is implanted into the peritoneal space through an incision in the epidermis 63, abdominal wall and parietal peritoneum using surgical techniques known to surgeons skilled in the art. The dialyzer assembly includes a triple lumen catheter 11 having a subcutaneous cuff 61 and a deep cuff 65 as illustrated in FIG. 10, which also shows a plurality of bowel loops 68 to further illustrate placement of the dialyzer element 72. The dialyzer element includes a filter membrane in diffusive contact with the transfer medium. Triple lumen catheter 11 is connected to dialyzer element 10 and provides fluid communication to the system. A first lumen 12 is connected to a fresh dialysate supply source 26 and directs the fresh dialysate into the interior dialysate passageway of the dialyzer element 10. A second lumen 14 is for directing toxic dialysate fluid from the dialyzer element. A third lumen 16 of catheter 11 is for filling the peritoneal cavity with the dialysis fluid transfer medium and to drain it periodically. Bacterial filters 13, 17 and 19, as well as the dialyzer membranes are composed of membranes with pores small enough to prevent passage of bacteria and virus are permanently attached to the outside terminal of each lumen to prevent contamination of the system with such organisms. Pumps 22 and 23 are used for pumping the dialysate to and from the dialyzer element. The pumps are preferably reciprocating pumps such as peristolic pumps, well known to those skilled in the art. However, any other suitable pumps or pumping means cooperating with the catheter 11 for supplying and removing dialysate fluid may be used. A drain bag or receptacle 28 receives and collects toxic dialysate from the outlet lumen 14 of the catheter. Optionally, a regeneration cartridge 24 may be used in the system for absorbing and removing toxins to form substantially fresh dialysate which then may be routed to the dialysis supply source 26 as illustrated. A suitable cartridge such as a redy-type cartridge known to those skilled in the art may be used.

The system illustrated in FIG. 1 preferably includes a microprocessor controller 78 for receiving signals 76 from pressure transducers 73 and 75 in the dialysate input and output passageways of a catheter and for sending control signals 74 to the pumps 22 and 23. The controller 78 is thus able to manage the system through monitoring of the flows in the inlet and outlet passageways via the transducers, and for operating the pumps to maintain a desired dialysate flow into and out of the dialyzer element 10. A modem 77 allows communication with a care giver via a communication line 79.

Once the dialyzer element 10 and portion of catheter 11 is implanted as generally illustrated in FIG. 10, the continuous peritoneal cascade dialysis process of the invention may be initiated. First, approximately 2 liters of fresh dialysate is introduced into the peritoneal cavity, and is allowed to dwell for a suitable time sufficient to allow the transfer medium to become substantially equilibrated with blood toxins contained in the surrounding peritoneal membrane vasculature. A typical initial dwell time will be between about 30 minutes and about 2 hours. After the initial dwell time, the continuous dialysis begins by pumping fresh dialysate fluid from the dialysate supply 26 through inlet lumen 12 to the dialyzer element 10. The fresh dialysate directed into the dialyzer element has a substantially zero concentration of toxins. The dialyzer element is provided with an interior dialysate passageway within a filter membrane having pores sufficient to allow diffusion of the toxins from the transfer medium through the pores to the dialysate passing along the interior passageway in the dialyzer element. Because the filter membrane of the dialyzer element is in diffusive communication or contact with the transfer medium, the dialysate within the passageway gradually becomes saturated with the blood toxins in the transfer medium. The toxin laden dialysate is then pumped out of the dialyzer element 10 via catheter lumen 14, through bacteria filter 17 and ultimately to drain bag 28, or to the dialysate supply 26 via a regeneration cartridge 24.

During the continuous pumping and removal of the dialysate fluid into, through and from the dialyzer element 10, it is important to regulate or maintain the rate of fluid movement through the interior dialysate passageway so that it will become substantially equilibrated with toxins in the transfer medium. The specific rate will depend on a number of parameters, including the patient's condition, diet, medication, condition of kidney function, etc., but is generally between about 5 ml and about 50 ml per minute. For many patients, a dialysis flow rate of about 30 ml/min is ideal. The length of treatment will depend on a number of other factors as will be discussed further hereinafter.

During the aforesaid continuous peritoneal dialysis process, fluid control and accordingly weight control of the patient depends on the creation of an osmotic gradient between the plasma and the transfer medium. Glucose is added to the dialysate and is as an effective and safe osmotic agent. Using controlled synchronous action, the two dialysate pumps 22 and 23 implement a uniform pressure, along the dialysate passageway within the filter membrane of the dialyzer element 10 and thus permit maintenance of a negative pressure with respect to the transfer medium 15 (FIG. 1) to facilitate peritoneal ultrafiltration for the purpose of body fluid control. However, as an alternative, the peritoneal ultrafiltrate may also be drained by means of the third lumen 16 of the catheter 11. It is important to periodically drain the transfer medium fluid from the peritoneal cavity to prevent long-term formation of deleterious protein compositions. The management of such aspects of the dialysis will be understood and adequately performed by those skilled in the art.

Figure 3:
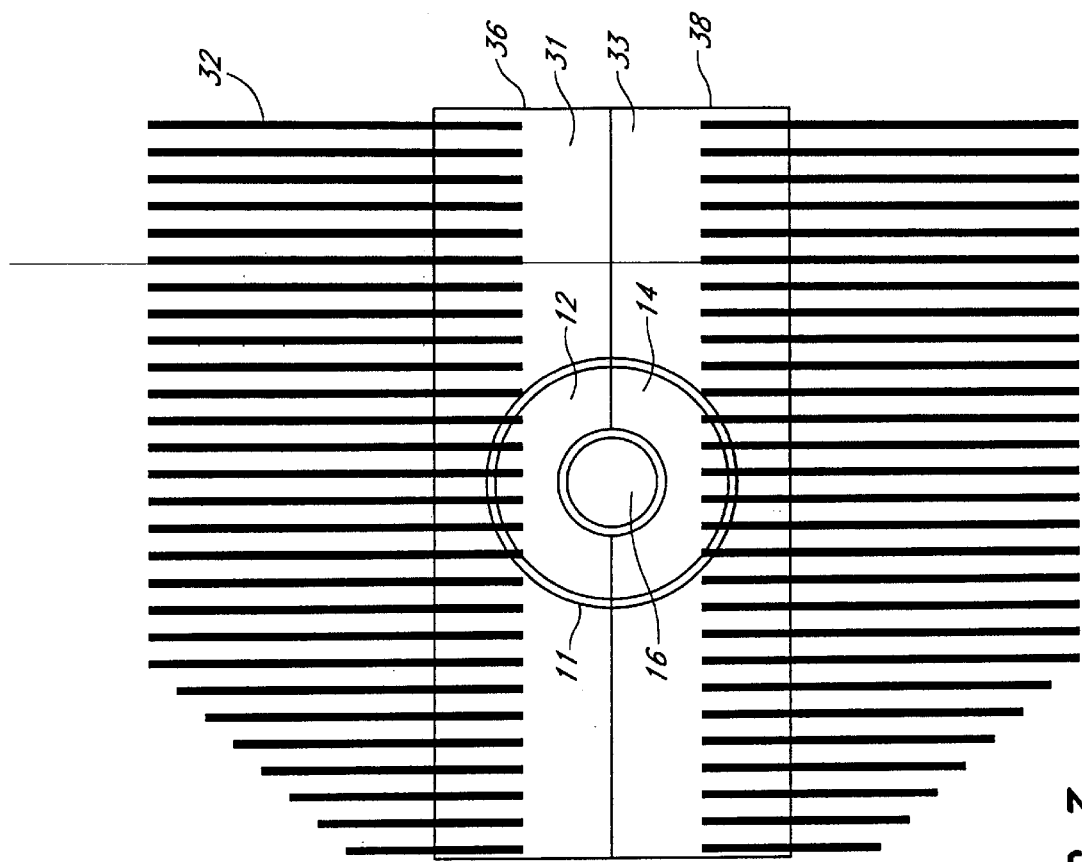
Figure 2:
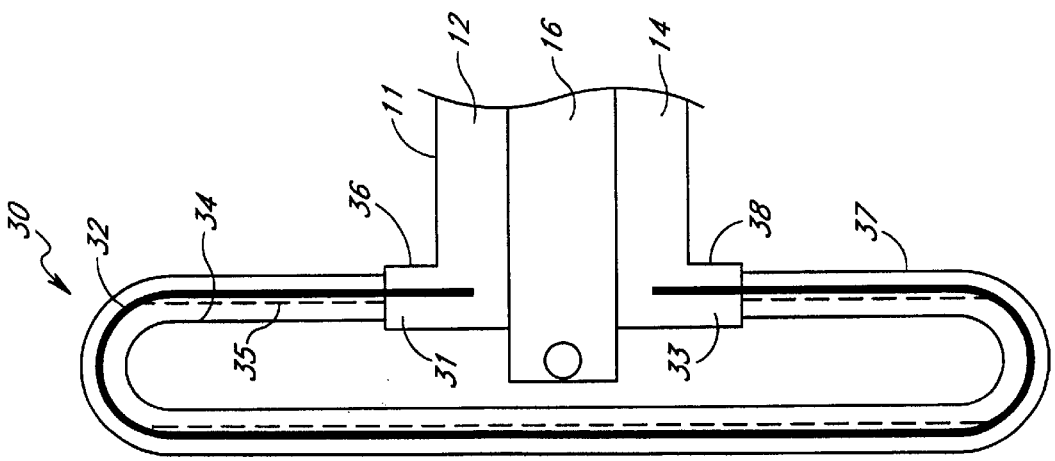
FIG. 2 is a side view and FIG. 3 a partial top view of one embodiment of the dialyzer element components and construction.

The components and construction of the in vivo dialysis element 10 shown in FIG. 1 may have a number of alternative designs and features. In FIGS. 2 and 3, a hollow fiber construction is used with one end of long hollow fibers potted into an inlet header 36 and the opposite end into an outlet header 38. The fibers are shaped into elongated flattened circle or ovals as shown in FIG. 2. The dialyzer element 30 shown includes an outer row of fibers 32 and an inner row 34 separated by a inner guard mesh 35. The hollow fibers comprise a membrane having a transmembrane flux and sieving coefficient design to meet prescription requirements as will be discussed hereinafter. Inlet header 36 includes an inlet passageway 31 communicating with inlet lumen 12 of triple lumen catheter 11. Outlet passageway 33 and outlet header 38 communicates with outlet lumen 14 of the catheter. The number of hollow fiber loops used in the dialysis element will depend on the desired size of the element as well as its filtration capacity. Thus, any number of such hollow fiber loops 32 may be used, again, with two rows being illustrated, although any number of such rows may be used. It is most desirable to include an outer guard mesh 37, coated with an anti-adhesion chemical for protecting the fibers from abrasion, and inhibiting adhesion to peritoneal wall membranes. The inner guard mesh 35 of similar design separates the inner and outer row of fiber loops to prevent contact and shading of the membranes by each other. The guard mesh is of highly porous woven or non-woven material having a low resistance to fluid flow. Such a feature promotes full communication between the transfer medium and the fiber membrane surface and free fluid passage between all the fibers. The shape of the total assembly may be modified by sequentially shortening portions adjacent loops as is illustrated in FIG. 3. The fibers are preferably coated with a polyethylene glycol or a siloxane and silver composition for improving the surface, i.e., smoothness, anti-adhesion, lubricity, biocompatibility and rejection of bacteria, and/or an anti-clotting material such as heparin.

The hollow fiber membranes used are preferably made of currently approved dialysis membrane material such as polyethersulphone, polycarbonate, nylon, polypropylene, etc. The size of the fiber membrane may be selected from between about 100 microns to about 500 microns in diameter, with wall thicknesses of 5 to 100 microns. Sieving coefficient zero cut-off points should be selected from $10^3$ daltons to $10^5$ daltons molecular weight. Suppliers of these dialysis membrane materials include Akzo-Nobel, Millipore, Inc., Poretics, Inc., and Pall Corp., by way of example. The interior of each of the hollow fibers 32 and 34 form an interior dialysate passageway within the filter membrane of the dialyzer element. Since the filter membrane pores are of sufficient size to allow diffusion of the blood toxins through the walls, as the fresh dialysate from the source is directed or pumped. into the input header 36 via inlet passageway 31 and inlet lumen 12, the dialysate directed through and along the interior length of each of the hollow fibers gradually becomes laden with toxins from the fluid transfer medium in contact with each of the hollow fiber membranes. As previously discussed, the flow rate of the dialysate between the inlet and outlet ends of the hollow fibers is such that the dialysate will become substantially equilibrated with the toxin concentrations in the transfer medium whereby the toxic dialysate withdrawn at the opposite fiber ends via outlet passageway 33 and outlet lumen 14 is substantially equilibrated with the toxin level or concentration in the transfer medium.

Figure 4:
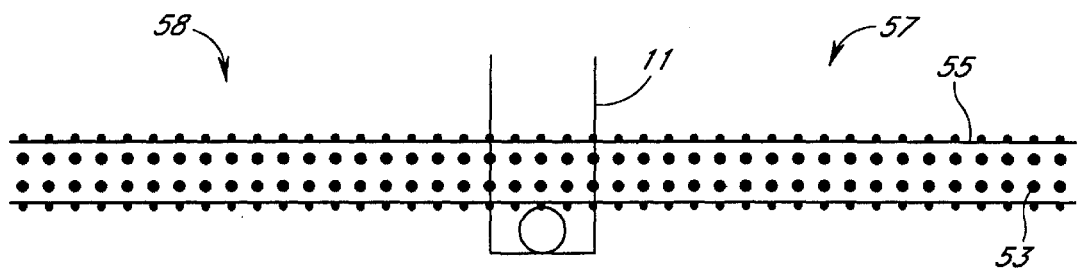
FIGS. 4 and 5 are a side view and top view, respectively, of another dialyzer element incorporating fibers.
Figure 5:
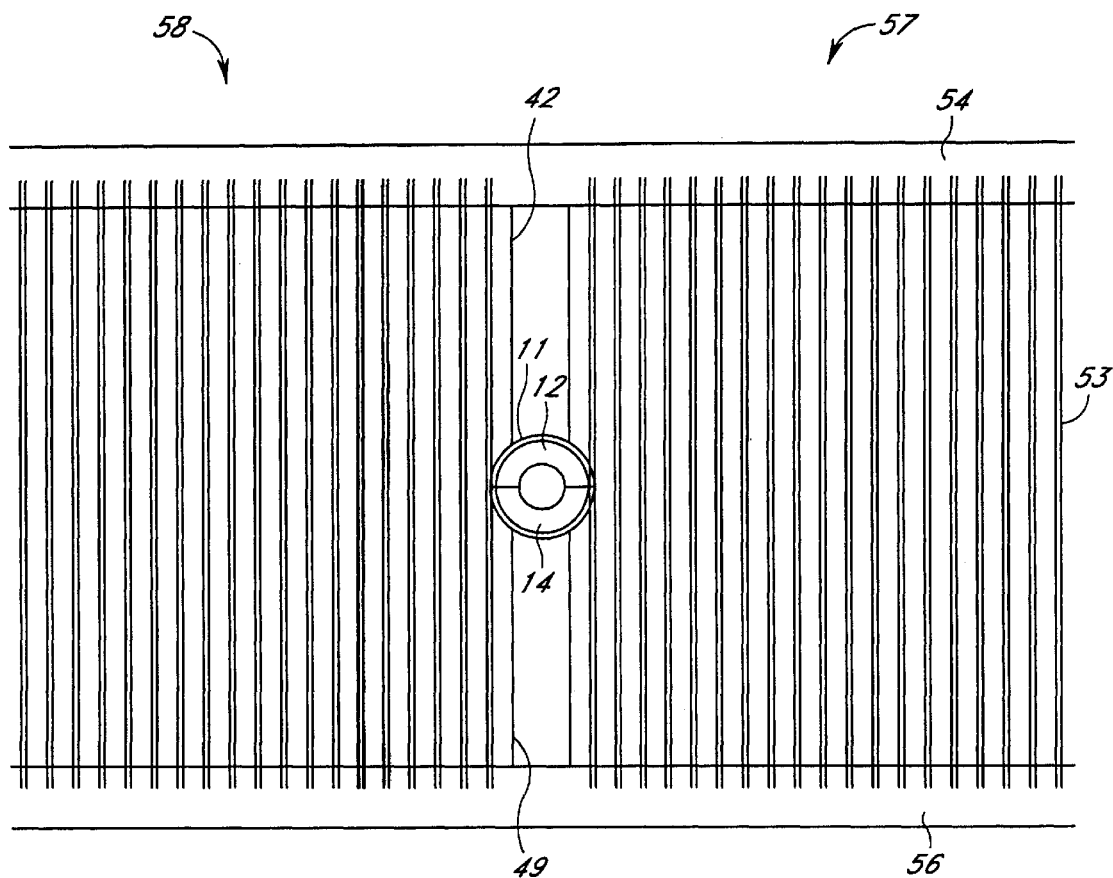

Another alternative construction of a dialyzer element 40 is illustrated in FIGS. 4 and 5. Such a configuration allows extension of the dialysis membrane over a larger surface area within the peritoneum. The dialyzer filter element includes an ascending lobe 57 and a descending lobe 58 each of which are in communication with triple lumen catheter 11. Hollow fibers 53 extend between an inflow header 54 and an outflow header 56. The two lobes of fibers achieve the required length by having parallel dialysis inflow and outflow headers 54 and 56, respectively, extending the length of the assembly. Inlet header 42 communicating with inlet catheter lumen 12 directs fresh dialysate header 48 into one end of the hollow filter membranes 53 and outlet feeder header 49 communicates between outlet header 56 and outlet lumen 14 of the catheter. The headers are preferably potted using polyurethane and are highly flexible to permit accommodation to the contours of the peritoneum. Both ends of the hollow fiber membranes 53 are potted into the respective headers to provide diffusive fluid communication with the transfer medium. Again, the membrane assembly of the type illustrated may be made up of any number of individual fibers suitably spaced for free fluid communication with the transfer medium to which they are exposed.

Two rows of fibers are illustrated in this embodiment, although any number of such rows may be used. The entirely assembly is surrounded by a guard mesh 55 as previously described to protect the hollow fiber membranes from damage and to prevent adherence to adjoining tissue.

A third alternative dialyzer element embodiment is illustrated in FIGS. 6 and 7, FIG. 6 showing a side view and FIG. 7 a partial top view of the element. In this embodiment, sheet filter membranes are used instead of the hollow fiber loop membranes previously described. As shown in FIG. 6, a top membrane sheet 46 and bottom membrane sheet 44 cover passageways 52 formed by separators or plates 45. An inlet header 43 communicates with dialysis inlet lumen 12 of catheter 11 forming an inlet passageway 42. An outlet header 48 forms an outlet passageway 47 with outlet lumen 14 of the catheter. Fresh dialysate is directed into the passageways via inlet port 82 and after passing through the tortuous path defined by the multiple separators or plates 45 is directed to outlet port 84, outlet passageway 47 and outlet lumen 14 of catheter 11. A plurality of baffles 51 may also be used to increase the length of the tortuous path the dialysate fluid must pass between the inlet and outlet ports, thereby improving the exposure efficiency of the fluid to the transfer medium with which the membranes 44 and 46 are in contact. Again, a guard mesh 41 is used to protect the membranes from damage and. adherence to peritoneal tissue. The sieve coefficient and membrane pore size as well as the materials used for the membrane sheets in the embodiments of FIG. 6 and 7 is the same as those previously described regarding the hollow fiber membranes.

Figure 9:
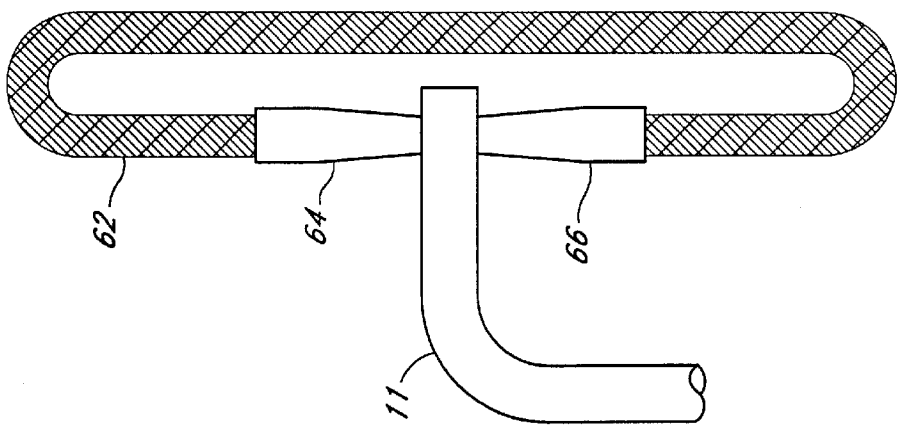
Figure 8:
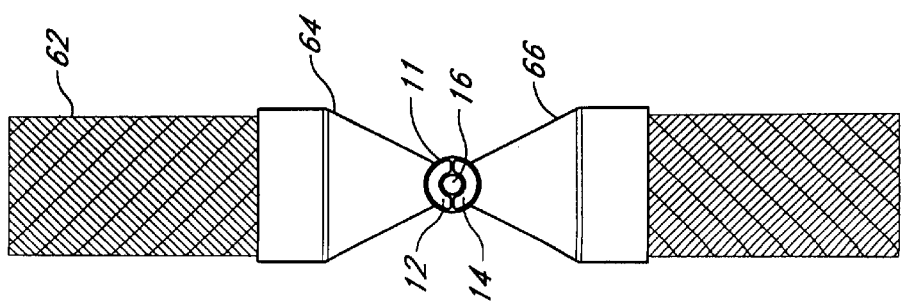
FIG. 8 is a top view and FIG. 9 a side view of yet another dialyzer element embodiment incorporating interlaced mesh bundles of hollow fibers.

FIGS. 8 and 9 illustrate top and side views of a hollow fiber dialyzer element in which the hollow fibers are interlaced in a mesh bundle 62. Headers 64 and 66 communicate with the ends of the bundled hollow fiber meshes, and communicate ex-vivo via catheter 11.

Figure 12:
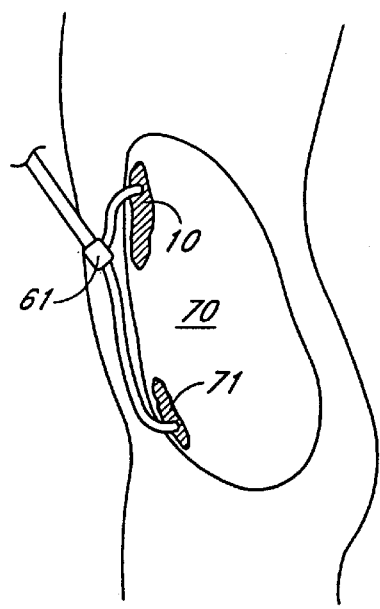
Figure 13:
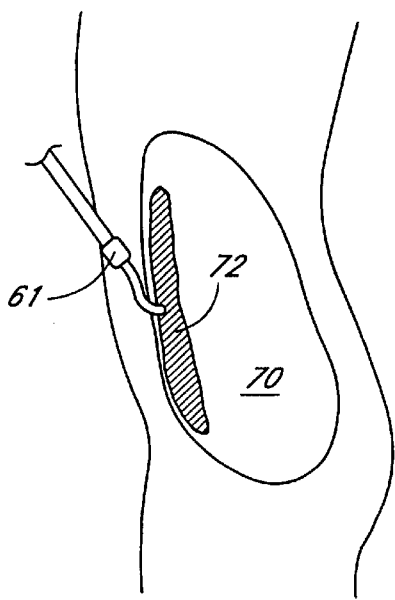

FIGS. 11, 12 and 13 illustrate different dialyzer element implant embodiments. Referring also to FIG. 10, FIG. 11 shows a single element 10 implanted in the peritoneal cavity 70 near the lower area of the peritoneal cavity, which may be most suitable for continuous dialysis where the patient is in an upright position most of the time during the dialysis treatment. FIG. 12 illustrates two dialysis elements, element 10 in the upper area of the peritoneal cavity and element 71 in the lower area. Such placement of multiple elements may be used to accommodate patients who choose to dialyze at night while in the supine position or who are nonambulatory. Positioning of the elements in the upper and lower areas or segments of the peritoneal cavity may ensure better contact with the transfer medium to obtain maximized fluid concentration exposure. In FIG. 13, a single elongated dialysis element such as is illustrated in FIGS. 4 and 5 having ascending and descending lobes extending over most of the anterior peritoneal cavity may be beneficial for other patients. Such figures illustrate variations of the use of the elements which may be selected to meet various medical and physiological requirements of the individual patient as well as the requirements of prescription protocols of the nephrologist.

Figure 14:
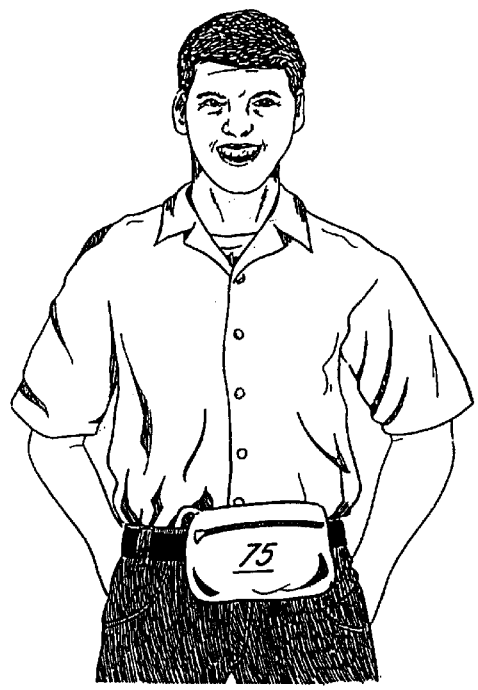
FIG. 14 illustrates a patient with an ex-vivo ambulatory system for carrying out the continuous peritoneal dialysis of the invention.

In FIG. 14, there is shown a "fanny pack" 75 containing a miniaturized dialyzing system of the invention which may be inconspicuously worn to accommodate the life-style of an active patient while maintaining continuing dialysis. Alternatively, the system may be designed to accommodate and fit in an undergarment vest which can be worn by the patient throughout the dialysis. Such embodiments are clearly substantially improved over the currently practiced continuous cycle peritoneal dialysis (CCPD) which requires a patient to be immobilized next to a machine for 6–8 hours of the procedure.

The system and its components as described hereinabove, as well as the resulting method of utilizing the system in carrying out continuous peritoneal dialysis offer a number of substantial and significant improvements over present or current dialysis methods. By making the process truly continuous, the invention improves the overall efficiency of peritoneal dialysis by as much as 230% over the typical ordinary continuous ambulatory peritoneal dialysis (CAPD). The current peritoneal dialysis therapy dialyses blood on the average of 30 minutes out of 70 minutes for each cycle, with the remaining 40 minutes required for draining used dialysate and infusing fresh dialysate. The process of the present invention dialyses blood for the full 70 minutes of the cycle thereby reducing the overall time required to carry out dialysis on the patient. Moreover, CAPD as presently practiced, requires seven or more 2 liter exchanges every day, creating a bothersome logistic burden on the patient as well as time consuming and awkward search for privacy to make periodic drainage and infusion of fluid.

The method of the invention permits a truly continuous dialysis of blood with the dialysate having a near zero concentration of toxins. The diffusion gradient between blood and dialysate is thereby maximized with corresponding maximization of toxin extraction as compared with conventional peritoneal dialysis processes involving an exponential increase in the concentration of dialysate toxins during the dwell time of the fluid in the peritoneum substantially reducing the effective diffusion gradient and toxin transfer.

Another significant improvement of the present invention is the ability of the filter membrane of the dialyzer element to provide a second cascade dialyzer function. Such a feature permits selective removal or retention of any of the plasma proteins having a molecular weight between $10^5$ daltons and $10^3$ daltons, a list of which is provided in Table 1. Such a feature obviates potential problems caused by the removal of important immune proteins as well as critical amounts of albumin. As previously disclosed, the peritoneal membrane acts as a plasmapheresis filter which allows the passage of blood and plasma components below $10^5$ daltons into the peritoneal cavity. Accordingly, the filter membrane of the dialyzer element of the present invention allows for selective removal or retention of plasma components between $10^3$ and $10^5$ daltons molecular weight, where such components are desired to be retained in the transfer medium and not discarded along with the toxin laden dialysate. Such an advantage avoids expensive and debilitating conditions such as hypoalbuminemia caused by prior conventional batch process peritoneal dialysis.

The present invention also provides a triple bacterial and viral barrier in the communication pathway between the exposure to ex-vivo conditions and fluids traversing the peritoneum. Thus, contrary to previously used methods, the present invention substantially reduces the risk of peritonitis and other infections commonly associated with conventional peritoneal dialysis methods which require breaking of the sterile barrier each time fluid is added or removed, several times a day.

Because the present invention permits total flexibility of continuous therapy in differing qualities and quantities in order to meet a patient's need for toxin clearance, scheduling of such therapy is available to fit the patient's activities, without penalty to optimum medical treatment or patient convenience. Such an advantage is possible because of the ability of the present method to program the flow of dialysate through the system to fit the overall toxin clearance protocol by adjusting flow rates and time and length of treatment.

The performance of kidney dialysis by any means is presently judged nephrologists by the formula Kt/V where Kt is the total plasma urea clearance in liters and V is the total body fluid in liters as shown in the body fluid compartments shown in FIG. 1. Kt also equals the sum of Kr (residual kidney function), Kd (dialysis clearance) and Ku (fluid loss by ultra filtration) in liters/day. Ideal Kt/V for hemodialysis is currently considered to be 1.3/day. Ideal Kt/V for peritoneal dialysis is currently considered to be 1.9/week. Table 2 shows weekly Kt/V calculations for systems using the present invention. It is expected that at a dialysis flow rate of 35 ml/min the ideal could be achieved in six hours or less of treatment per day and at a worse case of 10 ml/min continuous treatment would exceed the ideal performance.

TABLE 1

BLOOD AND PLASMA COMPONENTS
SIZE BY MOLECULAR WEIGHT (DALTONS)

| COMPONENT | $\leq 10^3$ DAL. | $\leq 10^4$ DAL. | $\leq 10^5$ DAL. | $\leq 10^6$ DAL. | $\geq 10^6$ DAL. |
|---|---|---|---|---|---|
| ELECTROLYTES | | | | | |
| $H_2O$ | 18 | | | | |
| Sodium | 22.89 | | | | |
| Magnesium | 24.3 | | | | |
| Chloride | 35.4 | | | | |
| Potassium | 39.1 | | | | |
| Calcium | 40.0 | | | | |
| NaCl | 58.5 | | | | |
| Urea | 60.0 | | | | |
| Glysine (smallest amino acid) | 75.0 | | | | |
| Creatinine | 113.1 | | | | |
| Uric Acid | 168.1 | | | | |
| Glucose | 180 | | | | |
| Dextrose | 180.1 | | | | |
| Triptophane (largest amino acid) | 204.2 | | | | |
| Sucrose | 342 | | | | |
| Billirubin | 584.6 | | | | |
| Haptens | $<1 \times 10^3$ | | | | |
| PROTEINS (74 g/L mean-adults) | | | | | |
| *Low flux Dialyzer cut-off* | | | | | |
| Inulin | | $5 \times 10^3$ | | | |
| Amyloid A protein | | $8 \times 10^3$ | | | |
| $\beta_2$-Microglobulin | | | $1.18 \times 10^4$ | | |
| Lisophospholipase | | | $1.3 \times 10^4$ | | |
| IL-2 Interleukin | | | $1.55 \times 10^4$ | | |
| CD3 (T3ξ) membrane complex | | | $1.6 \times 10^4$ | | |
| Myoglobin | | | $1.76 \times 10^3$ | | |
| J-chain | | | $1.76 \times 10^4$ | | |
| IL-5 Interleukin | | | $1.8 \times 10^4$ | | |
| M-CSF | | | $1.8 \times 10^4$ | | |
| Serum amyloid A component | | | $2.0 \times 10^4$ | | |
| IL-4 Interleukin | | | $2.0 \times 10^4$ | | |
| CD3 (T3ξ, ε) membrane complex | | | $2.0 \times 10^4$ | | |
| IL-6 Interleukin | | | $2.1 \times 10^4$ | | |
| Retinol binding protein | | | $2.12 \times 10^4$ | | |
| $C_8 \gamma$ complement protein | | | $2.2 \times 10^4$ | | |
| IL-3 Interleukin-3 | | | $2.2 \times 10^4$ | | |
| Factor D | | | $2.4 \times 10^4$ | | |
| Flagellin | | | $2.5-6 \times 10^4$ | | |
| CD3 (Tγ) membrane complex | | | $2.5 \times 10^4$ | | |
| $\alpha_1$ - Microglobulin | | | $2.5-3.3 \times 10^4$ | | |
| Cls Complement protein | | | $2.7 \times 10^4$ | | |
| Class II histocompatibility molecules | | | $2.7-3.4 \times 10^4$ | | |
| CD3 (T3 ω) membrane complex | | | $2.8 \times 10^4$ | | |
| G-CFS | | | $3.0 \times 10^4$ | | |
| 9.5 S-α Glycoprotein | | | $3.08 \times 10^4$ | | |
| Li Invariant chain | | | $3.1 \times 10^4$ | | |
| IL-1 Interleukin-a | | | $3.1 \times 10^4$ | | |
| Urokinase Low H form | | | $3.3 \times 10^4$ | | |
| Thrombin | | | $3.3 \times 10^4$ | | |
| $C_{3d}$ complement protein | | | $3.3 \times 10^4$ | | |
| Apolipoprotein E | | | $3.3 \times 10^4$ | | |
| Erythropoietin | | | $3.4 \times 10^4$ | | |
| $\beta_2$-Glycoprotein III | | | $3.5 \times 10^4$ | | |
| Transcobalamin II | | | $3.8 \times 10^4$ | | |
| Factor I β | | | $3.8 \times 10^4$ | | |
| Interferon γ | | | $4.0 \times 10^4$ | | |
| $Z_n.\alpha_2$-Glycoprotein | | | $4.1 \times 10^4$ | | |
| Actin filaments | | | $4.2 \times 10^4$ | | |
| Protein A | | | $4.2 \times 10^4$ | | |
| Class I histocompatibility molecule | | | $4.4 \times 10^4$ | | |
| $\alpha_1$-Acid glyoprotein | | | $4.41 \times 10^4$ | | |
| M-CSF | | | $4.5 \times 10^4$ | | |
| $\alpha_1$-Antitrypsin | | | $4.5 \times 10^4$ | | |
| CD1 Membrane glycoprotein | | | $4.6 \times 10^4$ | | |
| Fab Fragment | | | $4.7 \times 10^4$ | | |
| *High flux Dialyzer cut-off* | | | | | |
| Factor VII Proconvertin | | | $5.0 \times 10^4$ | | |
| $\beta_2$-Glycoprotein I | | | $5.0 \times 10^4$ | | |
| $\alpha_1$ B Glycoprotein | | | $5.0 \times 10^4$ | | |

TABLE 1-continued

BLOOD AND PLASMA COMPONENTS
SIZE BY MOLECULAR WEIGHT (DALTONS)

| COMPONENT | $\leq 10^3$ DAL. | $\leq 10^4$ DAL. | $\leq 10^5$ DAL. | $\leq 10^6$ DAL. | $\geq 10^6$ DAL. |
|---|---|---|---|---|---|
| Factor I α | | | $5.0 \times 10^4$ | | |
| Transcortin | | | $5.07 \times 10^4$ | | |
| CD 2 membrane glycoprotein T lymph. | | | $5.0–5.8 \times 10^4$ | | |
| LMK kininogen | | | $5.0–6.8 \times 10^4$ | | |
| Ge-Globulin | | | $5.2 \times 10^4$ | | |
| Urokinase high M form | | | $5.4 \times 10^4$ | | |
| Thromboplastin Factor III | | | $5.6 \times 10^4$ | | |
| Properdin | | | $5.6 \times 10^4$ | | |
| Factor X Stuart-Prower factor | | | $5.6 \times 10^4$ | | |
| Factor IX Plasma thromboplastin | | | $5.7 \times 10^4$ | | |
| Factor AtIII Heparin cofactor | | | $5.8 \times 10^4$ | | |
| Hemopexin | | | $5.7 \times 10^4$ | | |
| Cls Complement protein α | | | $5.8 \times 10^4$ | | |
| α-Antichymotrypsin | | | $5.8 \times 10^4$ | | |
| 3.8S-α-glycoprotein | | | $5.8 \times 10^4$ | | |
| Hemofilter cut-off | | | | | |
| α$_2$HS-Glycoprotein | | | $5.9 \times 10^4$ | | |
| α$_1$ T-Glycoprotein | | | $6.0 \times 10^4$ | | |
| Proalbumin | | | $6.1 \times 10^4$ | | |
| Prothrombin | | | $6.27 \times 10^4$ | | |
| α$_2$-Antiplasmin | | | $6.3 \times 10^4$ | | |
| Thiroxine-binding globulin | | | $6.3 \times 10^4$ | | |
| C$_8$ α,β complement protein | | | $6.4 \times 10^4$ | | |
| CD 5 membrane glycoprotein | | | $6.5 \times 10^4$ | | |
| Klenow fragment | | | $6.8 \times 10^4$ | | |
| Hemoglobin | | | $6.8 \times 10^4$ | | |
| α$_1$X-Glycoprotein | | | $6.8 \times 10^4$ | | |
| Protein S | | | $6.9 \times 10^4$ | | |
| Albumin | | | $6.9 \times 10^4$ | | |
| DAF decay accelerator | | | $7.0 \times 10^4$ | | |
| α$_2$-Aniti plasmin | | | $7.0 \times 10^4$ | | |
| C9 Complement component | | | $7.1 \times 10^4$ | | |
| t_PA Tissue plasminogen activator | | | $7.2 \times 10^4$ | | |
| Dextran | | | $7.5 \times 10^4$ | | |
| C5,C4,C3 Complement component β | | | $7.5 \times 10^4$ | | |
| Factor XII Hageman factor | | | $8.0 \times 10^4$ | | |
| Hemepoxin | | | $8.0 \times 10^4$ | | |
| C$_{1r}$ complement protein | | | $8.3 \times 10^4$ | | |
| Kallikrein | | | $8.8 \times 10^4$ | | |
| Interferon gamma receptor | | | $9.0 \times 10^4$ | | |
| Transferrin | | | $9.0 \times 10^4$ | | |
| Hmk kininogen | | | $8–11.4 \times 10^4$ | | |
| β$_2$-Glycoprotein II | | | $9.3 \times 10^4$ | | |
| C4 Complement component α | | | $9.3 \times 10^4$ | | |
| Sex binding Globulin | | | $9.4 \times 10^4$ | | |
| Fab$_2$ fragment | | | $9.5 \times 10^4$ | | |
| CR4 Complement receptor | | | $9.5–15 \times 10^4$ | | |
| Factor B | | | | $1 \times 10^5$ | |
| CALLA glycoprotein | | | | $1 \times 10^5$ | |
| Haptoglobin | | | | $1 \times 10^5$ | |
| DNA polymerase 1 | | | | $1.03 \times 10^5$ | |
| C1 Inh glycoprotein | | | | $1 \times 10^5$ | |
| HMWK Kininogen | | | | $1.1 \times 10^5$ | |
| C7 Complement component | | | | $1.04 \times 10^5$ | |
| C1 inhibitor | | | | $1.05 \times 10^5$ | |
| C4 binding protein | | | | $1.07 \times 10^5$ | |
| C2 Complement | | | | $1.08 \times 10^5$ | |
| C-reactive protein | | | | $1.1 \times 10^5$ | |
| Integrins | | | | $1.1–1.3 \times 10^5$ | |
| E-LAM 1 adhesion molecule 1 | | | | $1.15 \times 10^5$ | |
| C5 Complement component α | | | | $1.15 \times 10^5$ | |
| C3 α | | | | $1.17 \times 10^5$ | |
| C$_6$ complement protein | | | | $1.24 \times 10^5$ | |
| Globulins (average) | | | | $1.4 \times 10^5$ | |
| CR2 Complement receptor | | | | $1.45 \times 10^5$ | |
| Factor H | | | | $1.5 \times 10^5$ | |
| IgG Immuneoglobulin | | | | $1.5 \times 10^5$ | |
| CR3 α Complement receptor | | | | $1.55 \times 10^5$ | |
| Factor XI (PTA) | | | | $1.6 \times 10^5$ | |
| Cefuloplasmin | | | | $1.6 \times 10^5$ | |
| IgA Immuneoglobulin | | | | $1.6 \times 10^5$ | |
| γG-Immuneoglobulin | | | | $1.6 \times 10^5$ | |
| IgD Immuneogloblin | | | | $1.75 \times 10^5$ | |

TABLE 1-continued

BLOOD AND PLASMA COMPONENTS
SIZE BY MOLECULAR WEIGHT (DALTONS)

| COMPONENT | ≤$10^3$ DAL. | ≤$10^4$ DAL. | ≤$10^5$ DAL. | ≤$10^6$ DAL. | ≥$10^6$ DAL. |
|---|---|---|---|---|---|
| Clathrin | | | | $1.8 \times 10^5$ | |
| Inter-α-trypsin inhibitor | | | | $1.8 \times 10^5$ | |
| IgE Immuneogloblin | | | | $1.9 \times 10^5$ | |
| Plasma filter cut-off | | | | | |
| Carcinoembryonic antigen | | | | $2.0 \times 10^5$ | |
| P complement (properdin) | | | | $2.2 \times 10^5$ | |
| CR1 Complement receptor | | | | $2.5 \times 10^5$ | |
| Fibronectin | | | | $2.5 \times 10^5$ | |
| Factor XIII Fibrin stabalizing factor | | | | $3.2 \times 10^5$ | |
| Factor V Proaccelerin | | | | $3.3 \times 10^5$ | |
| Cholinesterase | | | | $3.4 \times 10^5$ | |
| Fibrinogen | | | | $4.0 \times 10^5$ | |
| Cold insoluble globulin | | | | $4.5 \times 10^5$ | |
| α-$_1$ Lipoprotein HDL$_3$ | | | | $1.9 \times 10^5$ | |
| HDL$_2$ | | | | $4.5 \times 10^5$ | |
| RNA polymerase | | | | $4.5$–$5 \times 10^5$ | |
| α$_2$-Macroglobulin | | | | $8.2 \times 10^5$ | |
| C1 complex | | | | $9 \times 10^5$ | |
| IgM Immuneogloblulin | | | | $9.55 \times 10^5$ | |
| β-Lipoprotein (LDL) | | | | | $3.2 \times 10^6$ |
| α$_2$-Lippoprotein (LDL) | | | | | $5$–$20 \times 10^6$ |
| Factor VIII antihemophilic globulin | | | | | $8.3 \times 10^6$ |
| Lymphocyte | | | | | >$10^6$ d = 8–12 μm |
| Megakaryocyte | | | | | >$10^6$ d = 35–160 μm |
| Lymphoid NK cells | | | | | d = 15 μm |
| Plasma cells | | | | | d = 14 μm |
| Platelet | | | | | d = 2–4 μm |
| Polymorphonuclear leukocyte | | | | | d = 13 μm |
| Erythrocytes | | | | | d = 7.5 μm |
| HIV virus Retroviridae | | | | | d = 80–130 nm |
| HBV virus Hepadnaviridae | | | | | d = 40 nm |
| CMV virus Herpesviridae | | | | | d = 150–200 nm |
| HCV virus Flaviridae | | | | | d = 40–50 nm |
| MuLV virus | | | | | d = 80–120 nm |
| Polio virus | | | | | d = 23–30 nm |
| Herpes Simplex virus | | | | | d = 120–150 nm |
| Aadenovirus | | | | | d = 70–90 nm |

TABLE 2

Kt/V BY DIALYSIS RATE AND TIME (Vd = 40000 ML)

| ml/min | 1 hr | 6 hrs | week | Kt/V | liters 8 hr | week | Kt/V | liters 16 hr | week | Kt/V | liters 24 hr | liters | |
|---|---|---|---|---|---|---|---|---|---|---|---|---|---|
| 10 | 600 | | | | 4800 | 33600 | 0.84 | 9600 | 67200 | 1.68 | 14400 | 100800 | 2.52 |
| 15 | 900 | | | | 7200 | 50400 | 1.26 | 14400 | 100800 | 2.52 | | | |
| 20 | 1200 | | | | 9600 | 67200 | 1.68 | | | | | | |
| 25 | 1500 | 9000 | 63000 | 1.575 | 12000 | 84000 | 2.1 | | | | | | |
| 30 | 1800 | 10800 | 75600 | 1.89 | 14400 | 100800 | 2.52 | | | | | | |
| 35 | 2100 | 12600 | 88200 | 2.205 | | | | | | | | | |

What is claimed is:

1. A system for continuous intraperitoneal dialysis comprising:

a dialyzer element for being implanted within the peritoneal cavity of a patient and comprising a filter membrane comprising a plurality of elongated hollow microporous fibers having an exterior membrane surface for being exposed to fluid within said peritoneal cavity and an interior membrane surface forming an interior dialysate passageway, said filter membrane having pores sufficient to allow diffusion of blood toxins therethrough;

an inlet for directing dialysate fluid into said dialyzer element and an outlet for directing dialysate fluid from said dialyzer element;

a tube having a first conduit connected to said inlet and a second conduit connected to said outlet; and one or more pumps cooperating with said tube for pumping dialysate fluid in and/or out of said dialyzer element.

2. A system of claim 1 further comprising one or more bacteria filters cooperating with said outlet or said second conduit for filtering dialysate fluid directed from said dialyzer element.

3. A system of claim 1 wherein said inlet comprises a header secured to said tube, said header having an inlet channel for directing dialysate from said first conduit to said interior dialysate passageway and an outlet channel for directing dialysate fluid from said interior dialysate passageway to said second conduit.

4. A system of claim 1 wherein said tube includes a third conduit for supplying transfer fluid to a patient's peritoneal cavity exteriorly of said interior dialysate passageway.

5. A system of claim 1 wherein said dialyzer element includes a porous guard secured around the exterior of said element and forming a protective envelope for said hollow fibers.

6. A system of claim 1 wherein each of said hollow fibers has a first end secured to said inlet and a second end secured to said outlet.

7. A system of claim 1 comprising a plurality of layers of said hollow fibers and including a porous guard separating adjacent fiber layers.

8. A system of claim 1 comprising a woven mesh of said hollow fibers.

9. A system of claim 1 wherein said fibers are coated with one or more compositions selected from polyethylene glycols, siloxanes and heparin.

10. A system for continuous intraperitoneal dialysis comprising:
 a dialyzer element for being implanted within the peritoneal cavity of a patient, and capable of filtering blood and plasma toxins exclusively by direct diffusive contact with peritoneal fluid present in the peritoneal cavity, said dialyzer element comprising:
  (i) a filter membrane consisting of a plurality of elongated hollow microporous fibers or one or more microporous membrane sheets, said filter membrane having pores of a size for selective removal or retention of toxins and components of between $10^3$ and $10^5$ daltons molecular weight, said filter membrane having an exterior membrane surface for being a direct diffusive contact with peritoneal fluid present in the peritoneal cavity, and an interior dialysate passageway for receiving dialysate fluid,
  (ii) an inlet for directing dialysate fluid to the interior dialysate passageway and an outlet for directing dialysate fluid from the dialyzer element, and
  (iii) a tube assembly comprising a first conduit connected to said inlet and a second conduit to said outlet.

11. A system of claim 10 wherein said inlet comprises a header secured to said tube, said header having an inlet channel for directing dialysate from said first conduit to said interior dialysate passageway and an outlet channel for directing dialysate fluid from said interior dialysate passageway to said second conduit.

12. A system of claim 11 wherein said filter membrane comprises a plurality of elongated hollow microporous fibers the hollow interior thereof forming said interior dialysate passageway, each of said hollow fibers having a first end secured to said inlet channel of said header and a second end secured to said outlet channel of said header.

13. A system of claim 12 wherein said dialyzer element includes a porous guard secured around the exterior of said element and forming a protective envelope for said hollow fiber.

14. A system of claim 13 comprising a plurality of layers of said hollow fibers and including a porous guard separating adjacent fiber layers.

15. A system of claim 12 wherein said fibers are coated with one or more compositions selected from polyethylene glycols, siloxanes and heparin.

16. A system of claim 10 wherein said filter membrane comprises a plurality of elongated hollow microporous fibers and wherein the hollow interior of said fibers comprises said interior dialysate passageway.

17. A system of claim 16 wherein said dialyzer element includes a porous guard secured around the exterior of said element and forming a protective envelope for said hollow fibers.

18. A system of claim 17 comprising a plurality of layers of said hollow fibers and including a porous guard separating adjacent fiber layers.

19. A system of claim 16 wherein each of said hollow fibers has a first end secured to said inlet means and a second end secured to said outlet means.

20. A system of claim 16 comprising a woven mesh of said hollow fibers.

21. A system of claim 16 wherein said fibers are coated with one or more compositions selected from polyethylene glycols, siloxanes and heparin.

22. A system of claim 10 wherein said filter membrane comprises one or more microporous membrane sheets and wherein said interior dialysate passageway is formed therebetween.

23. A system of claim 22 wherein said interior dialysate passageway includes means for creating a tortuous passageway for said dialysate fluid for at least a portion of the length of said interior dialysate passageway.

24. A system of claim 23 wherein said means comprises a plurality of plates forming a plurality of channels along said passageway.

25. A system of claim 23 wherein said means comprises a plurality of baffles positioned along said passageway.

26. A system of claim 22 wherein said inlet means comprises a header secured to said tube, said header having an inlet channel for directing dialysate from said first conduit to said interior dialysate passageway and an outlet channel for directing dialysate fluid from said interior dialysate passageway to said second conduit.

27. A system of claim 22 wherein said one or more membrane sheets are coated with one or more compositions selected from polyethylene glycols, siloxanes and heparin.

28. A system of claim 10 further comprising one or more bacteria filters cooperating with said inlet or said first conduit for filtering dialysate fluid directed into said dialyzer element.

29. A system of claim 28 further comprising one or more bacteria filters cooperating with said outlet or said second conduit for filtering dialysate fluid directed from said dialyzer element.

30. A system of claim 28 wherein said one or more pumps comprises a peristolic pump.

31. A system of claim 10 wherein said filter membrane has a pore size allowing passage of blood and plasma toxins having a molecular weight of less than $10^5$ daltons and selected plasma proteins having a molecular weight between $10^3$ and $10^5$ daltons.

32. A system of claim 31 wherein said selected molecular weight is less than about $7.0 \times 10^4$ for preventing passage of albumin through said membrane.

33. A system of claim 10 further comprising:
one or more pumps cooperating with said tube assembly for pumping dialysate fluid in and/or out of said dialyzer element.

34. A system of claim 10 including a dialysate fluid supply cooperating with said first conduit for supplying fresh dialysate fluid thereto.

35. A system of claim 10 including a receptacle cooperating with said second conduit for receiving toxic dialysate fluid from said dialyzer element.

36. A system of claim 10 wherein said dialyzer element comprises a filter membrane having a pore size allowing passage only of materials having a molecular weight of less than $10^3$ daltons.

37. A system of claim 10 wherein said tube includes a third conduit for supplying transfer fluid to a patient's peritoneal cavity exteriorly of said interior dialysate passageway.

38. A system of claim 10 wherein said tube comprises a triple lumen catheter having a third conduit therein terminating exteriorly from said interior dialysate passageway.

* * * * *